United States Patent [19]
Anderson et al.

[11] Patent Number: 5,905,164
[45] Date of Patent: May 18, 1999

[54] POLYALKYLENE POLYOL ESTERS OF DIALKYLAMINOBENZOIC ACID AND THEIR USE IN PHOTOINITIATED CURING PROCESSES

[75] Inventors: David George Anderson, Skelton; Robert Stephen Davidson; Neil Richard Cullum, both of Canterbury; Elizabeth Sands, London, all of United Kingdom

[73] Assignee: Lambson Fine Chemicals Limited, Castleford, United Kingdom

[21] Appl. No.: 08/930,581

[22] PCT Filed: Apr. 17, 1996

[86] PCT No.: PCT/GB96/00910

§ 371 Date: Feb. 27, 1998

§ 102(e) Date: Feb. 27, 1998

[87] PCT Pub. No.: WO96/33157

PCT Pub. Date: Oct. 24, 1996

[30] Foreign Application Priority Data

Apr. 18, 1995 [GB] United Kingdom ............... 9507808

[51] Int. Cl.⁶ .................. C07C 229/00; C07C 205/00
[52] U.S. Cl. ................................. 560/50; 560/20
[58] Field of Search .......................... 560/20, 50

[56] References Cited

U.S. PATENT DOCUMENTS 4,515,981  5/1985  Kozo et al. .

FOREIGN PATENT DOCUMENTS

| 0 003 872 | 9/1979 | European Pat. Off. . |
| 0 023 315 | 2/1981 | European Pat. Off. . |
| 0 042 486 | 12/1981 | European Pat. Off. . |
| 0 570 838 | 11/1993 | European Pat. Off. . |
| 22 55 910 | 5/1974 | Germany . |
| 22 60 151 | 6/1974 | Germany . |
| 306 565 | 6/1955 | Switzerland . |
| 326 786 | 2/1958 | Switzerland . |
| 2 010 888 | 7/1979 | United Kingdom . |
| WO 95 04118 | 2/1995 | WIPO . |

OTHER PUBLICATIONS

Chemische Berichte, vol. 117, 1984, Weinheim DE, pp. 1994–1997, XP002010498, E. Bayer et al., "Darstellung von Monound Divinylethern des Tetra (oxyethylens)".

Journal Of The American Chemical Society, vol. 62, 1940, DC US, pp. 3136–3139, XP002010499, J.F. Manning, "Solid Derivatives of Monoalkyl Ethers of Ethylene Glycol and Diethylene Glycol. II", see p. 3137—p. 3138; table II.

Journal Of The American Chemical Society, vol. 62, No. 7, 1940, DC US, pp. 1635–1640, XP002010500, P. Mason et al., "Solid Derivatives of Monoalkyl Ethers of Ethylene Glycol and Diethylene Glycol".

Pharm. Weekbl. (1969), 104(26), 658–70 Coden: PHWEAW, 1969, XP000578904, Buechi, Jakob et al., "Synthesis and antitussive activity of some 3–butoxy–4–amino–benzoic acid esters".

Patent Abstracts Of Japan, vol. 18, No. 668 (C–1289) & JP,A, 06 263814 (Toyo Ink Mfg. Co. Ltd), cited in the application.

*Primary Examiner*—Brian M. Burn
*Assistant Examiner*—Brian J. Davis
*Attorney, Agent, or Firm*—Nikaido Marmelstein Murray & Oram LLP

[57] ABSTRACT

Amine compounds of general formula (I),

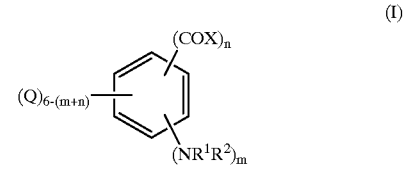

wherein: each $R^1$ independently represents an alkyl group; each $R^2$ independently represents an alkyl group; each group X independently represents a polyalkylene polyol moiety wherein hydroxyl groups of the polyol moiety are optionally alkylated but not including a group X which includes an ethyleneoxy or di(ethyleneoxy) moiety; n and m independently represent 1, 2 or 3; and each Q is independently selected from hydrogen or halogen atoms, and alkyl, acyl, nitro, cyano, alkoxy, hydroxy, amino, alkylamino, sulphinyl, alkylsulphinyl, sulphonyl, alkylsulphonyl, sulphonate, amido, alkylamido, alkoxycarbonyl, halocarbonyl and haloalkyl groups, processes for their preparation and intermediate compounds are described. Compounds of general formula (I) are useful as radiation curing agents in polymerisation processes.

20 Claims, No Drawings

POLYALKYLENE POLYOL ESTERS OF DIALKYLAMINOBENZOIC ACID AND THEIR USE IN PHOTOINITIATED CURING PROCESSES

This invention relates to novel amine compounds, to their preparation, to their use as radiation curing agents in polymerisation processes, and to polymeric products cured by such amine compounds.

Amines, especially tertiary amines, are important curing agents for photoinitiated curing processes. They are used in conjunction with photo-excited species, commonly called photoinitiators, which react with the amines to generate amine-derived radicals which initiate polymerisation.

There are two commercially important aromatic amine curing agents currently available, ethyl-4-(N,N'-dimethylamino) benzoate (EDB) and 2-n-butoxyethyl 4-(dimethylamino) benzoate (BEDB). These are highly effective as curing agents when used in conjunction with thioxanthone initiators, in particular isopropylthioxanthone (ITX). However they suffer the disadvantage that they tend to migrate from the polymer, over time. The surface of the polymer may be spoiled and compounds may migrate into the substrate, which could, for example, be a food or drinks products.

Japanese published patent application 6263814 (Toyo Ink) discloses curing agents obtained by reacting dihydric polyol compounds, for example ethylene glycol, with dimethylaminobenzoic acid. These are used in curable coating compositions said to have reduced odor, and to be free from deterioration from curability. However, in experiments we have found such curing agents to be rather slow in inducing polymerisation; and to migrate from a cured polymer at an unacceptably high rate.

It is an object of the present invention to provide an amine curing agent which is effective in inducing polymerisation and which is effectively retained within the cured polymer. That is to say, its migration from the cured polymer is to be low, or nil.

In accordance with a first aspect of the present invention, there is provided an amine compound of the general formula

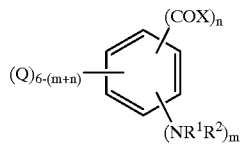

(I)

wherein:
each $R^1$ independently represents an alkyl group;
each $R^2$ independently represents an alkyl group;
each group X independently represents a polyalkylene polyol moiety wherein hydroxyl groups of the polyol moiety are optionally alkylated;
n and m independently represent 1, 2 or 3; and
each Q is independently selected from hydrogen or halogen atoms, and alkyl, acyl, nitro, cyano, alkoxy, hydroxy, amino, alkylamino, sulphinyl, alkylsulphinyl, sulphonyl, alkylsulphonyl, sulphonate, amido, alkylamido, alkoxycarbonyl, halocarbonyl and haloalkyl groups.

Suitably, n and m independently represent 1 or 2 preferably 1.

Suitably, each Q represents a hydrogen atom.

Suitably, each $R^1$ represents the same alkyl group.
Suitably, each $R^1$ represents a $C_{1-4}$ alkyl group, preferably methyl.
Suitably, each $R^2$ represents the same alkyl group.
Suitably, each $R^2$ represents a $C_{1-4}$ alkyl group, preferably methyl.
Suitably, one or each group X includes at least two ether functionalities.
Suitably, each X independently represents a polyalkylene glycol moiety, wherein hydroxyl groups of the moiety are optionally alkylated.
Suitably, each X represents a polyethylene glycol moiety, wherein hydroxyl groups of the moiety are optionally alkylated.
Suitably, one or preferably each, group X represents a polyol moiety which is end-capped by an alkyl group.
Suitably, the alkyl group which end caps the group X is a $C_{1-4}$ alkyl group. Preferably, it is a methyl group.
Preferably, one or preferably each group X represents a polyol moiety wherein each hydroxyl group is alkylated.
Preferably, one or each group X is of the general formula —O—(CH$_2$—CH$_2$—O)$_z$-alkyl where z has a mean value of from 2 to 20, preferably 4 to 15, most preferably 6 to 13 and the alkyl group is suitably a $C_{1-4}$ alkyl group, preferably methyl.
Preferably, at least one said group COX is located para to a said dialkylamine group. Where n=m=1, preferably the group COX is located para to the dialkylamine group.

In accordance with a second aspect of the present invention there is provided a process for the preparation of a compound of general formula I, which process comprises alkylation of a corresponding primary amine compound (in which $R_1=R_2$=hydrogen). This may be carried out by reductive alkylation, using the appropriate alkanal.

Such a reaction can be carried out in a hydrogenator, at elevated temperature and pressure, and in the presence of hydrogen.

The corresponding primary amine compound can itself be prepared by similar hydrogenation, from the corresponding nitro compound.

The nitro compound may be easily prepared by reaction of the appropriate nitrobenzoic acid with the appropriate optionally alkylated polyol compound retaining at least one hydroxyl group. Alternatively, the appropriate nitrobenzoic acid chloride may be employed, suitably with a base, for example an amine base, suitably triethylamine.

In accordance with a third aspect of the present invention there is provided a process for the preparation of a compound of general formula I, which process comprises esterification of the appropriate dialkylamine benzoyl chloride compound, with the appropriate optionally alkylated polyol compound having at least one hydroxyl group. This reaction suitably takes place in the presence of a base, for example an amine base, for example triethylamine. This reaction suitably takes place at a temperature in the range −20° C. to 40° C., preferably 0° C. to ambient temperature. The benzoyl chloride reactant may be prepared by chlorination of the corresponding benzoic acid, for example using thionyl chloride, suitably at ambient temperature.

The invention further extends to any novel intermediates referred to herein, and to the methods for their preparation. Thus, the invention provides an intermediate compound of general formula

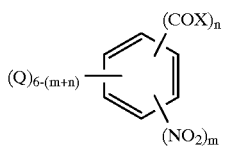

wherein X, Q, n and m are as described in any statement herein.

The invention also extends to an intermediate compound of general formula

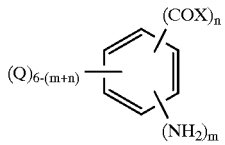

wherein X, Q, n and m are as described in any statement herein.

In accordance with a further aspect of the present invention there is provided a polymer curing composition, which may be in kit form, comprising a compound of general formula I as described above, together with a photoinitiator, the photoinitiator, when photo-excited, being able to react with the compound of general formula I to generate an amine-derived radical.

In accordance with a further aspect of the present invention there is provided a polymerisable composition comprising a polymerisable material suitably present in an amount from 80 to 97 wt. %, a compound of general formula I, suitably present in an amount from 14 to 2 wt. %, and a photoinitiator, suitably present in an amount from 6 to 1 wt. %.

In accordance with a further aspect of the present invention there is provided a polymeric composition derived from said polymerisable composition by photo-curing.

A suitable photoinitiator may, for example, be a thioxanthone compound, preferably isopropyl thioxanthone, or an anthroquinone compound, or a benzophenone compound. Preferably, however, it is a novel benzophenone of the type described in our co-filed patent application entitled "Novel Photoinitiators", the contents of which are incorporated herein by reference. Thus, such a benzophenone compound is of the general formula

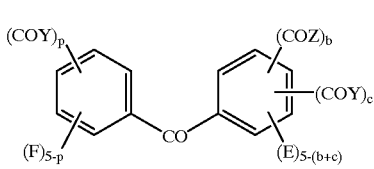

(II)

wherein:
each Z independently represents an alkylene polyol moiety or a polyalkylene polyol moiety, wherein hydroxyl groups of the polyol moiety are optionally alkylated;
each Y independently represents an alkylene polyol moiety or a polyalkylene polyol moiety, wherein hydroxyl groups of the polyol moiety are optionally alkylated; or an alkoxy group;
each E is independently selected from hydrogen or halogen atoms and alkyl, acyl, nitro, cyano, alkoxy, hydroxy, amino, alkylamino, sulphinyl, alkylsulphinyl, sulphonyl, alkylsulphonyl, sulphonate, amido, alkylamido, alkoxycarbonyl, halocarbonyl and haloalkyl groups;
each F is independently selected from hydrogen or halogen atoms and alkyl, acyl, nitro, cyano, alkoxy, hydroxy, amino, alkylamino, sulphinyl, alkylsulphinyl, sulphonyl, alkylsulphonyl, sulphonate, amido, alkylamido, alkoxycarbonyl, halocarbonyl and haloalkyl groups;
b represents 1 to 5;
c represents 0 to 4; and
p represents 0 to 5.

Suitably, b represents 1 or 2, preferably 1.
Suitably, c represents 0 or 1, preferably 0.
Suitably, each E represents a hydrogen atom.
Suitably, p represents 0 or 1.
Suitably, each F represents a hydrogen atom.
Suitably, one or each group Z includes at least two ether functionalities.

Suitably, the or each group Z independently represents an alkylene glycol or polyalkylene glycol moiety wherein hydroxyl groups of the moiety are optionally alkylated.

Suitably, the or each group Z represents an ethylene glycol or polyethylene glycol moiety, wherein hydroxyl groups of the moiety are optionally alkylated.

Suitably, one or preferably each, group Z represents a polyol moiety which is end-capped by an alkyl group.

Suitably, an alkyl group which end caps the group Z is a $C_{1-4}$ alkyl group. Preferably, it is a methyl group.

Suitably, one or preferably, each group Z represents a polyol moiety wherein each hydroxyl group is alkylated.

Suitably, one or preferably each group Z is of the general formula $—O—(CH_2—CH_2—O)_e$-alkyl where e has a mean value of from 2 to 20, preferably 4 to 15, most preferably 6 to 13 and the alkyl group is suitably a $C_{1-4}$ alkyl group, preferably methyl.

Preferably, a said group COY is located in the 2- or 4-position, most preferably in the 4-position.

Suitably, one or each group Y includes at least two ether functionalities.

Suitably, each Y independently represents an alkylene glycol or polyalkylene glycol moiety, wherein hydroxyl groups of the moiety are optionally alkylated.

Suitably, Y represents an ethylene glycol or polyethylene glycol moiety, wherein hydroxyl groups of the moiety are optionally alkylated.

Suitably, one or preferably each, group Y represents a polyol moiety which is end-capped by an alkyl group.

Suitably, an alkyl group which end caps the group Y is a $C_{1-4}$ alkyl group. Preferably, it is a methyl group.

Suitably, one or preferably, each group Y represents a polyol moiety wherein each hydroxyl group is alkylated.

Preferably, one or preferably each group Y is of the general formula $—O—(CH_2—CH_2—O)_e$-alkyl where e has a mean value of from 2 to 20, preferably 4 to 15, most preferably 6 to 13.

Preferably, a said group COY is located in the 2- or 4-position, most preferably in the 4-position.

Compounds of the general formula II, may be prepared by esterification or transesterification of a precursor benzophenone compound to the compound of general formula I, with the appropriate alkyl end-capped alkylene glycol compound, having a single hydroxyl group.

When p represents 0, the preferred reaction is an esterification, using the appropriate benzoyl benzoic acid.

When p represents 1 and Y represents an alkylene glycol or polyalkylene glycol moiety, end-capped by an alkyl group, the preferred reaction is a transesterification, preferably from the appropriate di(methoxycarbonyl) benzophenone compound.

When p represents 1 and Y represents an alkoxy group the favored reaction is an esterification, using the appropriate precursor compound having one ester group COY, where Y represents the alkoxy group, and one group —COOH.

The esterification/transesterification may be carried out under standard conditions. The esterification reaction may be carried out in an organic solvent, for example toluene, at an elevated temperature, preferably under reflux, with removal of water during the reaction process. Preferably, an acid, suitably an organic acid, for example a sulphonic acid, is present. Suitably a catalyst is present. A suitable catalyst is tin (II) octanoate. The transesterification reaction may be carried out in an organic solvent, for example toluene, in the substantial absence of water, at an elevated temperature, preferably under reflux. Preferably an acid, suitably an organic acid, for example a sulphonic acid, is present. Suitably a catalyst is present, preferably an alkyl titanate.

A suitable polymerisable material is any material whose polymerisation can be initiated by an amine radical. Preferably the polymerisation is applied to acrylate systems where the polymerisable material (monomer) may, for example be 1,6-hexanediol diacrylate (HDDA), 2-hydroxyethyl acrylate (HEA), hydroxypropyl acrylate (HPA) and methyl methacrylate (MMA).

The polymerisable materials may be suitable for surface/coating/film applications. They may be formulated with other components, including inks, for printing applications.

The invention will now be further described, by way of example.

Preparation of amine curing agents of the invention
Compound 1: 2-(2-methoxyethoxy)ethyl-4-N,N'-dimethylamino benzoate Firstly, 4-dimethylamino benzoylchloride was prepared. The reaction was accomplished by placing 4-dimethylamino benzoic acid (ex. Lancaster) (4.0 g, 24.22 mmol) in a 25 ml round bottom flask, to which was added thoinyl chloride (ex. Aldrich) (3.0 ml). This reaction mixture became orange immediately upon the addition of the thionyl chloride. The reaction mixture was stirred for 1 hour at ambient temperature, after which time the remaining thionyl chloride was removed under reduced pressure. The last trace of the thionyl chloride was removed by azeotroping with dry benzene (2×20 ml).

The brown/orange residue was then recrystallised from dry toluene (100 ml). After dissolving the residue, the solution was filtered and the filtrate dried with anhydrous sodium sulphate. It was again filtered and the solvent removed under reduced pressure until the initial emergence of the product. At this time the flask was removed from the rotary evaporator and the product allowed to crystallise out naturally. The crystals were collected under vacuum filtration and washed with dry diethyl ether (2×20 ml). The crystals were dried under vacuum.
Data:
Yield: 3.75 g; NMR $^1$H (60 MHz, DMSO-$d_6$/TMS) δ (ppm): 6.8–7.8 (m,Ar,4H); 2.95 (s,Me$_2$N,6H). IR (KBr ν cm$^{-1}$: Note the absence of —OH group between 3300–3500 (C—H), 1600 (C=O), 800 (Ar). $C_9H_{10}ONCl$
Microanalysis: Requires C: 58.86% H: 5.48% N: 7.62%
Found C: 58.20% H: 5.54% N: 7.52%
Melting point: 136–138° C.

To a round bottom flask equipped with a 50 ml dropping funnel, was added triethylamine (ex. Aldrich) (1.22 g, 1.1 mol equiv.). 2-(2-Methoxyethoxy)ethanol (ex. Aldrich) (1.22 g, 0.01 mol) was then added. The mixture was then dissolved in dry THF (20 ml). The flask was then placed in an ice bath and cooled to 0° C.

4-Dimethylamino benzoyl chloride (2.00 g, 0.01 mol) was also dissolved in dry THF (20 ml). This solution was placed in the dropping funnel, and added dropwise to the stirred, cooled solution below. After the final addition of the acid chloride the solution was allowed to stir for 17 hours at ambient temperature. The reaction was completed by removing the triethylamine hydrochloride by filtration, and the remaining solvent under reduced pressure. The residue that was left was redissolved in chloroform (50 ml) and washed with brine (15 ml). The organic layer was then removed and dried with sodium sulphate, filtered and the chloroform removed under reduced pressure. This yielded the title compound as a white/cream semi-solid, more solid than liquid.
Data:
Yield: 1.98 g; NMR $^1$H (100 MHz), CDCl$_3$/TMS) δ (ppm): 6.6–8.0 (m,Ar,4H); 4.3–4.5 (triplet,OCH$_2$CH$_2$,2H); 3.5–3.9 (m,CH$_2$—O—CH$_2$CH$_2$—O,6H); 3.4 (s,OMe,3H); 3.0 (s,NMe$_2$,6H). IR (KBr) ν cm$^{-1}$: 2780–3020 (C—H); 1700 (C—O); 1610 (C=O); 780 (Ar) $C_{14}H_{21}O_4N$
Microanalysis: Requires C: 62.90% H: 7.92% N: 5.24%
Found C: 61.34% H: 8.38% N: 5.18%
Homogeneity point: 45–50° C.
Extinction coefficient: 227700 @ 310.8 nm
Compound 2: 4-N,N'-dimethylaminobenzoyl poly(ethylene alycol)$_{350}$ monomethylether To a 25 ml round bottom flask equipped with a 50 ml dropping funnel was added triethylamine (ex. Aldrich) (1.22 g, 1.1 mol equiv.). Poly(ethylene glycol)$_{350}$ monomethyl ether (ex. Fluka) (3.38 g, 0.01 mol) was then added. The mixture was dissolved in dry THF (20 ml). The flask was then placed in an ice bath and cooled to 0° C.

4-Dimethylamino benzoyl chloride (2.00 g, 0.01 mol) was also dissolved in dry THF (20 ml). This solution was placed in the dropping funnel, and added dropwise to the stirred cooled solution below. After the final addition of the acid chloride the solution was allowed to stir for 17 hours at ambient temperature.

The reaction was completed by removing the triethylamine hydrochloride by filtration, and the remaining solvent under reduced pressure. The residue that was left was redissolved in chloroform (50 ml) and washed with brine (15 ml). The organic layer was then removed and dried with sodium sulphate, filtered and the chloroform removed under reduced pressure. This yielded the title compound as a yellow/brown semi-solid, more liquid than solid.
Data
Yield: 3.21 g; NMR $^1$H (100 MHz, CDCl$_3$/TMS) δ (ppm): 6.5–7.9 (m,Ar,4H); 3.6 (s,PEG,manyH[~28]; 3.3 (s,OMe, 3H); 3.0 (Me$_2$N—,6H). IR (KBr) ν cm$^{-1}$: 2800–2960 (C—H); 1700 (C—O); 1620 (C=O); 770 (Ar). $C_{24}H_{41\ O9}N$
Microanalysis: Requires C: 59.13% H: 8.42% N: 2.87%
Found C: 57.81% H: 8.77% N: 2.35%
Homogeneity point: 50–60° C.
Extinction coefficient: 215600 @ 310.8 nm
Compound 3: 4-N,N'-dimethylaminobenzoyl Poly(ethylene glycol)$_{350}$ monomethylether
Compound 4: 4-N,N'-dimethylaminobenzoyl Poly(ethylene glycol)$_{750}$ monomethylether Compounds 3 and 4 were synthesised using a similar method to each other, as follows.
Esterification of 4-nitrobenzoic acid The following reactants were placed in a 500 ml three necked round bottom flask equipped with a thermometer, overhead stirrer, and a Dean Stark apparatus with a condenser.

4-Nitrobenzoic acid (ex. Lancaster) (50.0 mg, 0.3 mol)/ (56.0 g, 0.33 mol)

Poly(ethylene glycol)$_{550}$ monomethyl ether (ex. Fluka) (181.0 g, 0.30 mol)

Poly(ethylene glycol)$_{750}$ monomethyl ether (ex. Fluka) (250.0 g, 0.33 mol)

Sulphuric acid 96% (2.60 g, 0.03 mol)/(3.4 g 0.035 mol) t-BAB (0.5 g)/(0.54 g) Toluene (100.0 ml)

The reaction mixtures were then heated to reflux while stirring. The heating was continued until all the water produced in the reactions had been azeotroped out by the toluene, (expected amount 6 ml, actual amount 5.8 ml). This took 5.5 hours, after which time the solutions were cooled and lime (CaCO$_3$~10 g) was added to neutralise the sulphuric acid and any excess 4-nitrobenzoic acid. The solutions were filtered under reduced pressure and the solvent removed under reduced pressure. This gave rise to a semi-solid brown product in both cases.

Hydrogenation of the nitro compounds

These reactions took place in a hydrogenator. 100 g of the respective PEG compound was dissolved in methanol (500 ml). Raney Nickel (Trade Mark) catalysts (10 g, 50% with water) were suspended in methanol (100 ml). To these were added 5 drops of acetic acid to ensure that the pH was at about 5.5.

The two solutions were then placed in the hydrogenator. This was maintained at 26° C. under 3 atmospheres of hydrogen and stirred at 600 rpm. After 16 hours the solutions were removed and the Raney Nickel catalysts were removed by filtration using a filter bed, under vacuum. The compounds were analysed using HPLC.

Reductive alkylation

The orange/yellow filtrates from the above reactions were again placed in the hydrogenator, along with the Raney Nickel catalyst (10 g, 50% with water) and para formaldehyde (10 g). The reaction mixtures were maintained at 50° C. under 3 atmospheres of hydrogen and stirred at 600 rpm for 72 hours. The solutions were then removed, filtered using the filter bed to remove all the catalyst and the solvents removed under reduced pressure. This yielded, in the case of the PEG 550, an orange/yellow semi-solid, and in the case of PEG 750, a waxy solid.

Data on Compound 3

Yield: 193.75 g; NMR $^1$H (100 MHz, CDCl$_3$/TMS) δ (ppm); 6.4–7.8 (m,Ar,4H); 3.6 (s,PEG,manyH[~48]); 3.0 (s,NMe$_2$,6H). IR (KBr) v cm$^{-1}$: 2700–3000 (C—H); 1700 (C—O); 1610 (C=O); 770 (Ar). C$_{34}$H$_{61}$O$_{14}$N Microanalysis: Requires C: 57.70% H: 8.62% N: 1.98%
Found C: 54.97% H: 9.18% N: 1.39%

Homogeneity point: 50–55° C.

Extinction coefficient: 171300 @ 310.0 nm

Data on Compound 4

Yield: 263.56 g; NMR $^1$H (100 MHz, CDCl$_3$/TMS) δ (ppm); 6.5–7.8 (m,Ar,4H); 3.7 (s,PEG,manyH[~64]); 3.4 (s,OMe,3H); 3.0 (s,NMe$_2$.,6H). IR (KBr) v cm$^{-1}$: 2700–3000 (C—H); 1700 (C—O); 1600 (C=O); 780 (Ar). C$_{42}$H$_{77}$O$_{18}$N Microanalysis: Requires C: 57.08% H: 8.72% N: 1.58%
Found C: 54.53% H: 9.63% N: 1.57%

Extinction coefficient: 127300 @ 296.1 nm

Comparison compounds

Compound C1: Ethyl dimethylamino benzoate

This is a commercially available product and for the tests described below was obtained from Lambson Fine Chemicals Limited of Castleford.

Compound C2: 2-n-Butoxyethyl 4-(dimethylamino) benzoate

This is a commercially available product and for the tests described below was obtained from Lambson Fine Chemicals Limited of Castleford.

Compound C3: Ethylene glycol di(4-methylaminobenzoate)

The above compound was synthesised by placing ethylene glycol (ex. Fisons) (0.169 g, 2.723 mmol) in a 100 ml round bottom flask. To this was added triethylamine (ex. Aldrich) (1.216 g, 2.2 mol equiv.) and THF (30 ml). Diethylamino benzoyl chloride (1.0 g, 5.446 mmol) was dissolved in dry THF (20 ml) and placed in a dropping funnel. The acid chloride was added dropwise to the cooled, stirred solution of ethylene glycol and triethylamine. After the last addition the solution was left for 17 hours, stirring at ambient temperature. The reaction was completed by removing the triethylamine hydrochloride by filtration from the solution. The remaining filtrate was then evaporated to dryness under reduced pressure. The residue was then dissolved in chloroform (50 ml) and the product washed with water (2×20 ml). The chloroform extract was then dried with anhydrous sodium sulphate, filtered and the chloroform removed under reduced pressure, to give a pale cream crystalline product.

Yield: 1.37 g; NMR $^1$H (270 MHz, CDCl$_3$/TMS) δ (ppm): 6.4–7.9 (m,Ar,8H); 4.5 (s,—CH$_2$CH$_2$—, 4H); 2.8 (s,2Me$_2$N—,12H). IR (KBr) v cm$^{-1}$: 2800–2960 (C—H); 1690 (C—O); 1610 (C=O); 760 (Ar) C$_{20}$H$_{24}$O$_4$N$_2$ Microanalysis: Requires C: 67.37% H: 6.78% N: 7.61%
Found C: 66.17% H: 6.71% N: 7.40%

Melting point: 171–174° C.

Compound C4: Poly(ethylene glycol)$_{300}$ di(4-dimethylamino benzoate)

Compound C5: Poly(ethylene glycol)$_{600}$ di(4-dimethylamine benzoate)

The preparation of the compounds C4 and C5 was afforded using the same method given for compounds 3 and 4 above.

Esterification of 4-nitrobenzoic acid

The following reactants were placed in a 500 ml round bottom flask equipped with a thermometer, overhead stirrer and a Dean Stark apparatus equipped with a condenser.

4-Nitrobenzoic acid (50.07 g, 0.3 mol, apx. ⅓ mole)/(100 g, 0.6 mol, apx. ⅓ mole)

Poly(ethylene glycol)$_{300}$ (49.40 g, 0.16 mol) /poly (ethylene glycol)$_{600}$ (200 g, 0.33 mol) t-BAB (0.5 g)/(0.5 g)

Sulphuric acid 96% (4.0 g, 0.04 mol) /4.4 g, 0.045 mol)

The respective mixtures were then stirred and azeotropically distilled to remove the water and form the respective esters (expected amount 12 ml, actual amount 11.8 ml). This took approximately 6 hours, after which time the solutions were cooled and lime added (CaCO$_3$~10 g) to neutralise the sulphuric acid and any remaining 4-nitrobenzoic acid that remained. The solutions were filtered and the solvent removed under reduced pressure.

Hydrogenation of nitro compounds

These reactions were carried out using a hydrogenator. The respective PEG compounds (100 g) were dissolved in methanol (500 ml). Raney Nickel catalysts (10 g, 50% with water) were suspended in methanol (100 ml). To these were added 5 drops of acetic acid to ensure that the pH was at about 5.5.

The two solutions were than placed in a hydrogenator. This was maintained at 20° C., under 3 atmospheres of hydrogen and stirred at 600 rpm. After 16 hours the solutions were removed and the Raney Nickel catalyst removed by filtration, using a filter bed under reduced pressure. The compounds were analysed using HPLC.

Reductive alkylation

The filtrates from the above reactions, suspended in methanol (100 ml), were placed in the hydrogenator, along with some more Raney Nickel catalyst (10 g, 50% with water) and para formaldehyde (10 g). The hydrogenator was maintained at 50° C., under 3 atmospheres of hydrogen and stirred at 600 rpm for 72 hours. The solutions were then removed, filtered using the filter bed to remove all the catalyst and the solvents removed under reduced pressure. This yielded, in both instances, an orange viscous liquid.

Data on Compound C4

Yield: 80.4 g; NMR $^1$H (10 MHz, CDCl$_3$/TMS) δ (ppm); 6.4–8.2 (m,Ar,8H); 3.7 (s,PEG,manyH[~28]); 3.1 (s,NMe$_2$., 12H). IR (KBr) ν cm$^{-1}$: 2800–3000 (C—H); 1700 (C—O); 1610 (C=O); 770 (Ar). $C_{32}H_{48}O_{10}N_2$ Microanalysis: Requires C: 61.93% H: 7.74% N: 4.52%

Found C: 59.89% H: 8.02% N: 3.97%

Extinction coefficient: 276600 @ 308.7 nm

Data on Compound C5

Yield: 235.84 g; NMR $^1$H (100 MHz, CDCl$_3$/TMS) δ (ppm); 6.6–8.1 (m,Ar,8H); 3.7 (s,PEG,manyH[~56]); 3.1 (s,NMe$_2$.,12H). IR (KBr) ν cm$^{-1}$: 2800–3000 (C—H); 1700 (C—O); 1600 (C=O); 770 (Ar). $C_{46}H_{76}O_{17}N_2$ Microanalysis: Required C: 59.48% H: 8.19% N: 3.02%

Found C: 57.37% H: 8.84% N: 2.82%

Extinction coefficient: 285200 @ 302.9 nm

Novel benzophenone initiators

As described below, isopropyl thioxanthone (ITX) was the photoinitiator used in most of the tests. However, also used were novel PEG-modified benzophenone photoinitiators, prepared as follows.

Compound A: 4-Benzoylbenzoyl poly(ethylene glycol)$_{350}$ monomethylether 2.1 g of poly(ethylene glycol)$_{350}$ mono methyl ether, 1 g of 4-benzoylbenzoic acid and 1 g of p-toluene sulphonic acid were refluxed with 100 ml of toluene until all water present had been driven over. Catalytic amounts of tin (II) octanoate were added and the mixture refluxed for 10 hours. After removal of the toluene, washing with sodium carbonate (to neutralise any free acid present) and drying under vacuum, a brown liquid was obtained (which became extremely viscous on standing). The product structure was confirmed by 100 MHz proton NMR.

Compound B: Di-[poly(ethylene glycol)$_{350}$ monomethylether] benzophenone-4,4'-dicarboxylate The first step was to prepare 4,4$^1$-dimethyl benzophenone. To do this, 25 ml of p-toluoyl chloride was added slowly to a stirred mixture of 30 g of anhydrous aluminium trichloride and 115 ml of dry toluene. The resulting solution was refluxed for 6 hours before the product was isolated by addition of the reaction solution to a solution of 200 ml water and 100 ml conc. HCl. The resulting red solid was distilled (short path) at 141° C. at 4 mm Hg. The distillate solidified on cooling to a white solid.

Melting point:=90–92° C.;

Elemental analysis: $C_{15}H_{14}O$;

requires % C=85.68, H=6.71;

found % C=85.66, H=6.44;

100 MHz proton NMR: solvent=CD$_2$Cl$_2$; aromatic protons 7–8 ppm AA$^1$BB$^1$ system (8H); methyl protons 2.4 ppm (6H).

The 4,4$^1$-dimethyl benzophenone was then oxidised to the corresponding dicarboxylic acid. A solution of glacial acetic acid and the 4,4$^1$-dimethyl benzophenone was added to a solution of aq. acetic acid (80% v/v) and chromium trioxide and stirred at ambient temperature for 24 hours. The addition of water facilitated a pale green precipitate. Isolation and H$^1$ NMR/elemental analysis showed partial oxidation. The reaction was driven to completion by refluxing, at 65° C., for 24 hours.

Elemental analysis: $C_{15}H_{10}O_5$ requires % C=66.67, H=3.74 found % C=66.71H=3.65

60 MHz H$^1$ NMR aromatic protons exhibiting an AA$^1$BB$^1$ splitting system 8–8.5 ppm.

% Yield=67.43%

FTIR exhibited a large —OH stretch (persisted after drying product in vacuum oven at 40° C. for 48 hours).

The dicarboxylic acid compound was esterified to form the dimethyl ester. The esterification was achieved by refluxing in methanol and an acid for 24 hours. The crude product was taken into THF and washed with water to remove free acid. Recrystallisation was from dry ethanol. Characterisation was by H$^1$ NMR which gave the AA$^1$BB$^1$ aromatic splitting pattern (8.20–8.70 ppm) and a singlet assigned to the methyl protons (4.20 ppm). Integration was in the ratio 4:3. FTIR exhibited no —OH stretch after drying.

Elemental analysis:

requires % C=68.45, H=4.73 found % C=68.67, H=4.54

Finally, the dimethyl ester was transesterified to form the title compound. 2.5 g Dimethyl ester, 6.25 g poly(ethylene glycol)$_{350}$ monomethylether and 50 ml of dry toluene was refluxed in a Dean and Stark apparatus for 1 hour. 0.25 g of Tilcom [Trade Mark—Ti(OPr)$_2$(OBu)$_2$] was injected and refluxing at 100° C. was continued for 4 hours. The methanol side product was removed using a fractionating column and the reaction was driven to completion by refluxing for a further 2.5 hours. Removal of the catalyst was achieved by addition of 2 ml of water to the vigorously stirred, cooled solution and filtration of the resulting precipitate of titanium oxide. The surplus water was removed by returning the toluene solution back to the Dean and Stark apparatus for 1 hour. Removal of the solvent produced a viscous, light brown liquid (yield c. 2 g).

Analysis:

60 MHz H$^1$ NMR; methyl ether 3.45 ppm singlet (6H) ethylene protons 3.75 ppm singlet (~58H) aromatic protons 7.95–8.50 ppm AA$^1$BB$^1$ (8H) HPLC; flow rate 1 ml/min, 254 nm, 20 micro liter sample loop, a 50/50 acetonitrile water mobile phase. The resulting trace showed two distinct groups of peaks, attributed to the mono and di-substituted PEG esters.

Note on microanalysis

It has been noted that the microanalysis (CHN) results on all compounds containing polyethylene glycol (PEG) are not as accurate as desired. This is not due to impurities in the compounds, but to the fact that PEG compounds contain average chain lengths. For example, a PEG compound of average molecular weight 350 contains chains that vary in between 2 and 12 ethylene glycol units. In order to calculate the percentage of carbon and hydrogen present in the chain it was necessary to determine the average number of units present. The method of calculating this is shown below.

PEG chain=350

Repeating unit (—OCH$_2$CH$_2$O—)=44.053

Mono methyl ether (OMe)=31.034

350–31.034=318.966

318.966 divided by 44.053=7.24

=~7 repeating units

Therefore, one can assess the number of carbon, hydrogen and oxygen atoms in the chain and it is also possible to calculate the overall number of individual carbon, hydrogen and oxygen atoms and hence the overall percentage composition.

Summary of Compounds

Compound 1
2-(2-methoxyethoxy)ethyl-4-N, N'-dimethylamino benzoate

Compound 2
4-N, N'-dimethylaminobenzoyl poly(ethylene glycol)$_{350}$ monomethylether

Compound 3
4-N, N'-dimethylaminobenzoyl poly(ethylene glycol)$_{350}$ monomethylether

Compound 4
4-N, N'-dimethylaminobenzoyl poly(ethylene glycol)$_{750}$ monomethylether

Compound C1
Ethyl dimethylamino benzoate

Compound C2
2-n-Butoxethyl 4-(dimethylamino) benzoate

Compound C3
Ethylene glycol di(4-methylaminobenzoate)

Compound C4
Poly(ethylene glycol)$_{300}$ di(4-dimethylamino benzoate)

Compound C5
Poly(ethylene glycol)$_{600}$ di(4-dimethylamino benzoate)

-continued

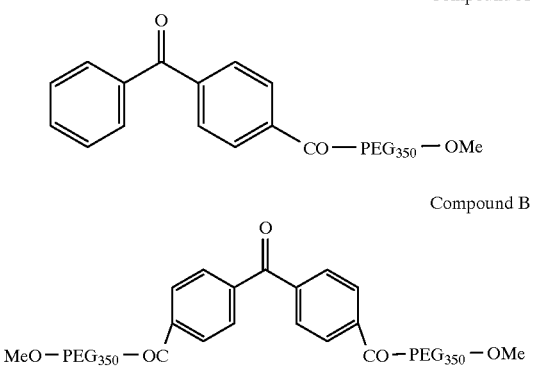

Compound A

Compound B

Effectiveness of Compounds as Curing Agents

For the purpose of these tests, unless otherwise stated, the standard pre-polymer mixture was as follows:

1–6 hexanediol acrylate (monomer): 93 wt %
amine curing agent: 5 wt %
isopropyl thioxanthone (ITX-photoinitiator): 2 wt %.

It was found that all of the compounds 1–4 and comparison compounds C1–C5 above, dissolved into such a pre-polymer mixture, except for comparison compound C1, which could not therefore be studied, and is without utility, at least in relation to the prepolymer mixture used for these tests.

Curing was by a medium pressure UV lamp. The results presented below relate firstly to the determination of whether the polymer cures and if so, how quickly; and, secondly, to the propensity of the amines to migrate from a polymer film after curing. The two methods employed to address these aspects were Real Time Infra Red (RT-IR) and High Pressure Liquid Chromography (HPLC).

Methods of Data Acquisition

RT-IR analysis of the rate of cure of each of the pre Polymer mixtures

The use if RT-IR allows the rate of cure of each of the samples to be analysed. This method allows an infra-red spectrum to be taken, then a frequency is chosen, one at which the transmittance would change during polymerisation. Commonly used is the acrylate stretch at 810 cm$^{-1}$, the acrylate double bonds disappearing during curing. Using the time drive facility, it allows infra-red analysis while the sample is being irradiated with a medium pressure UV lamp, thus allowing the increase in transmittance to be monitored. This gives an indication of the rate of polymerisation. A second spectrum was run. This showed the final position of the acrylate stretch.

Two RT-IR's were run on each pre-polymer mixture. The samples were prepared as follows. A drop of each pre-polymer mixture was placed between two polyethylene sheets in the center of a polyether spacer of 25 $\mu$m. This was to ensure that all the films were of the same thickness. This sandwiched sample was then placed between two NaCl plates, which in turn were placed in a holder unit. This entire unit was then placed into the infra-red machine and the spectrum run.

HPLC method used for analysing the Propensity of the amines to migrate

The method for testing the propensity of the amines to migrate was the same throughout.

The migratable amine content of each film was analysed as follows. Initially a drop of the pre-polymer mixture was placed on a piece of satinised paper. This was then evenly spread over the surface using a "K" bar which gave a film thickness of between 50–60 $\mu$m.

For each of the curing agents, samples of film were taken after:

i) No passes of the Colordry unit (i.e., the UV lamp)
ii) 2 passes of the Colordry unit.
iii) 4 passes of the Colordry lamp.
iv) 6 passes of the Colordry lamp.

The Colordry unit contains a medium pressure mercury lamp. The samples are placed on a moving belt (in these trials this was set at 24 meters/minute). It was important to ensure two main factors during this stage of the trial. Firstly, that all the samples taken, of satinised paper and film, were of the same size. It was for this reason that a metal template was made that gave samples of 21×28 mm. Secondly, that the curing of the film was as unaffected by oxygen inhibition as possible. This was ensured by placing the paper and uncured film in a cell with a quartz window. This cell was then evacuated with nitrogen and sealed. Only then was the sample passed through the Colordry unit.

The 21×28 mm samples of each pre-polymer mixture at 0, 2, 4 and 6 passes were then placed in individual 7 ml sample vials. To each vial was added 5 ml of a de-gassed acetonitrile/water 50/50 mix, enough to immerse each sample. The vials were then placed in a dark cupboard for 20 hours. After this time the vials were removed and the sample extracted from each vial. All that was left in each vial was the solvent containing the migratables that had leached out from the film in the 20 hour period.

Methods of Data Analysis

RT-IR analysis of the rate of cure of each of the ore polymer mixtures

For each sample three spectra were run, to allow an average to be taken. Each spectrum had a decay curve which represents the rate of polymerisation. The steeper the gradient of the curve, the faster the rate. The angle of the gradient was measured and this could then be used to compare the rate of polymerisation achieved by the different curing agents.

HPLC method used for analysing the migration of amines from films

These samples were then prepared for HPLC analysis by filtering each one using Sartorus Millistart 0.45 $\mu$m disposable filters. This was to ensure that there were no solid contaminants that would damage the HPLC column.

Chromographs of the amine components for each of the films were run prior to the trials. This was to ensure that firstly the elution time was known and, secondly, to determine whether the respective amine components had any characteristic shaped peaks.

After filtration each sample was injected on to the HPLC column. Each sample was run in acetonitrile/water 50/50 mixture. The data from each run was then used to analyse the migratable content of each film.

On the chromatogram for the solution containing migrated amine compounds, the area under each of the relevant peaks was noted.

It was assumed that the contents of the solution that had contained the film that had not passed the UV lamp, contained 100% migratable amine compound, because the pre-polymer mixture was not irradiated. The values for the areas under the peaks from the solutions that had contained films that had passed the UV lamp, 2, 4 and 6times could then be correlated respectively to the 100% migration value of the uncured solution.

Results

TABLE 1

RT-IR Trials

| Compound | RT-IR Data |
|---|---|
| 1 | 67° |
| 2 | 75° |
| 3 | 74° |
| 4 | 19° |
| C1 | 56° |
| C2 | 52° |
| C3 | inoperable |
| C4 | 50° |
| C5 | 18° |

The angles of gradient expressed are a measure of the decay curve which represents the rate of polymerisation. The steeper the gradient, the faster the rate of polymerisation.

TABLE 2

HPLC Migration Analysis

| Compound | % Amine Compounds | | | |
|---|---|---|---|---|
| | 0 | 2 | 4 | 6 |
| 1 | 100 | 27 | 25 | 12 |
| 2 | 100 | 0 | 0 | 0 |
| 3 | 100 | 12 | 0 | 0 |
| 4 | 100 | 73 | 56 | 21 |
| C1 | 100 | 42 | 41 | 25 |
| C2 | 100 | 67 | 54 | 25 |
| C3 | inoperable | | | |
| C4 | 100 | 42 | 20 | 15 |
| C5 | 100 | 38 | 18 | 13 |

It will be seen that by the use of preferred amines of the present invention, improved properties can be achieved, in terms of migration of the amines from the cured polymer, with the improvement being most marked for compounds 2 and 3 indicating a preferred mean molecular weight the PEG component of the -OPEGOMe chain, of around, 250–650. curing time is also very fast using compounds 1, 2 and 3 although slower for compound 4. Comparison between compounds 2 and C4 and between compounds 3 and C5, are of interest because of the closeness of the mean molecular weights of the PEG components between these pairs of compounds. The properties of compounds 2 and 3 are, surprisingly, significantly better than those of C4 and C5 respectively, both in terms of cure rate, and migration characteristics.

Further tests

Several curing agents were tested further, to assess their efficiency in polymerising HDDA. This was assessed using FTIR as described above.

Curing Agent 5%, photoinitiator 2%, HDDA 93% a) Ethyl-4-dimethylamino benzoate [EDB]/Compound A/HDDA b) Compound 2/Compound A/HDDA c) Compound 2/Compound B/HDDA Results Percentage transmittance at 810 cm$^{-1}$

| No. of UV passes | 0 | 2 | 4 | 6 |
|---|---|---|---|---|
| a | 7.79 | 61.74 | 63.42 | 60.97 |
| b | 13.06 | 60.24 | 65.63 | 60.23 |
| c | 12.48 | 53.43 | 59.83 | 70.15 |

It will be seen that the novel PEG-substituted initiators and curing agent provide good rates of reaction and high degrees of polymerisation, in addition to the good or excellent self-migration properties, shown by the other tests. The PEG-substituted initiators and PEG-substituted curing agent were fully compatible in the formulation.

The use of the amine curing agents of the type of compounds 1 to 4 can be expected to offer certain further advantages. Firstly, the use of the end-capped glycol can be expected to have a plasticizing effect, useful to increase the flexibility, and hence the durability, of films. Secondly, its incorporation may be expected to increase the compatibility of the amine compounds, with paper surfaces. When polymer films, cured using amine compounds, are used in conjunction with paper, the extra adherence is desirable. Thirdly, the compounds are likely to be highly soluble in water, such that the amine curing agents could be used in conjunction with aqueous curing formulations. These advantages are likely to be furthered, when the novel benzophenone initiators are also used.

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

We claim:

1. An amine compound of the General formula

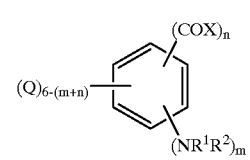

(I)

wherein:

each $R^1$ independently represents an alkyl group;

each $R^2$ independently represents an alkyl group;

each group X independently represents a polyalkylene polyol moiety wherein hydroxyl groups of the polyol moiety are optionally alkylated but not including a group X which includes an ethyleneoxy or di(ethyleneoxy) moiety;

n and m independently represent 1, 2 or 3; and each Q is independently selected from hydrogen or halogen atoms, and alkyl, acyl, nitro, cyano, alkoxy, hydroxy, amino, alkylamino, sulphinyl, alkylsulphinyl, sulphonyl, alkylsulphonyl, sulphonate, amido, alkylamido, alkoxycarbonyl, halocarbonyl and haloalkyl groups.

2. A compound according to claim 1, wherein n and m represent 1.

3. A compound according to claim 1, wherein each Q represents a hydrogen atom.

4. A compound according to claim 1, wherein each $R^1$ represents a $C_{1-4}$ alkyl group.

5. A compound according to claim 1, wherein each $R^2$ represents a $C_{1-4}$ alkyl group.

6. A compound according to claim 1, wherein one or each group X represents a polyol moiety which is end-capped by an alkyl group.

7. A compound according to claim 1 wherein one or each group X is of the general formula $-O-(CH_2-CH_2-O)_z$-alkyl where z has a mean value of from 6 to 13 and the alkyl group is a $C_{1-4}$ alkyl group.

8. A compound according to claim 1, wherein group X excluding any optional alkyl group has a molecular weight in the range 250–750.

9. A compound according to claim 1, wherein group X excluding any optional alkyl group has a molecular weight in the range 250–650.

10. A process for the preparation of a compound of general formula I according to claim 1, which process comprises alkylation of a corresponding primary amine compound.

11. A process for the preparation of a compound of general formula I according to claim 1, which process comprises esterification of the appropriate dialkylamine benzoyl chloride compound, with the appropriate optionally alkylated polyol compound having at least one hydroxyl group.

12. A polymer curing composition comprising a compound of general formula I as described in claim 1, together with a photoinitiator, the photoinitiator, when photo-excited, being able to react with the compound of general formula I to generate an amine-derived radical.

13. A polymerisable composition comprising a polymerisable material, a compound of general formula I as described in claim 1 and a photoinitiator.

14. A polymeric composition derived from said polymerisable composition of claim 13 by photo-curing.

15. A method of polymerising a polymerisable material, the method comprising combining a polymerisable material, a compound of general formula I as described in claim 1 and a photoinitiator to produce a polymerisable composition; and photo-curing the polymerisable composition to produce a polymeric composition, wherein the polymeric composition is produced at a rate of polymerisation, measured using Real Time Infra Red analysis, which is greater using the compound of general formula I as described in claim 1 than using a first comparative compound of formula I wherein n and m each represent 1, $R^1$ and $R^2$ each represent a methyl group, Q represents a hydrogen atom and X represents a methoxy end-capped polyethylene glycol-750 moiety.

16. A method of polymerising a polymerisable material, the method comprising combining a polymerisable material, a compound of general formula I as described in claim 1 and a photoinitiator to produce a polymerisable composition; and photo-curing the polymerisable composition to produce a polymeric composition, wherein the polymeric composition has an amine migration rate, measured using High Pressure Liquid Chromatography analysis, which is less using the compound of general formula I as described in claim 1 than using a first comparative compound of formula I wherein n and m each represent 1, $R^1$ and $R^2$ each represent a methyl group, Q represents a hydrogen atom and X represents a methoxy end-capped polyethylene glycol-750 moiety.

17. The method according to claim 15, wherein the polymeric composition has an amine migration rate, measured using High Pressure Liquid Chromatography analysis, which is greater using the compound of general formula I than using the first comparative compound of formula I.

18. The method according to claim 15, wherein the polymeric composition is produced at a rate of polymerisation, measured using Real Time Infra Red analysis, which is greater using the compound of general formula I than using a second comparative compound of formula I wherein n and m each represent 1, $R^1$ and $R^2$ each represent a methyl group, Q represents a hydrogen atom and X represents $-OCH_2OCH_2OMe$, and/or the polymeric composition has an amine migration rate, measured using High Pressure Liquid Chromatography analysis, which is less using the compound of general formula I than using the second comparative compound of formula I.

19. The method according to claim 16, wherein the polymeric composition is produced at a rate of polymerisation, measured using Real Time Infra Red analysis, which is greater using the compound of general formula I than using a second comparative compound of formula I wherein n and m each represent 1, $R^1$ and $R^2$ each represent a methyl group, Q represents a hydrogen atom and X represents $-OCH_2OCH_2OMe$, and/or the polymeric composition has an amine migration rate, measured using High Pressure Liquid Chromatography analysis, which is less using the compound of general formula I than using the second comparative compound of formula I.

20. The method according to claim 17, wherein the polymeric composition is produced at a rate of polymerisation, measured using Real Time Infra Red analysis, which is greater using the compound of general formula I than using a second comparative compound of formula I wherein n and m each represent 1, $R^1$ and $R^2$ each represent a methyl group, Q represents a hydrogen atom and X represents $-OCH_2OCH_2OMe$, and/or the polymeric composition has an amine migration rate, measured using High Pressure Liquid Chromatography analysis, which is less using the compound of general formula I than using the second comparative compound of formula I.

* * * * *